United States Patent [19]

Anchor

[11] Patent Number: 4,587,365

[45] Date of Patent: May 6, 1986

[54] PREPARING CAPPED POLYOXYALKYLENE POLYOLS

[75] Inventor: Michael J. Anchor, Canton Township, Wayne County, Mich.

[73] Assignee: BASF Corporation, Wyandotte, Mich.

[21] Appl. No.: 666,208

[22] Filed: Oct. 29, 1984

[51] Int. Cl.$^4$ .............................................. C07C 41/16
[52] U.S. Cl. .................................. 568/619; 568/607; 568/608; 568/609; 568/611; 568/618
[58] Field of Search ............... 568/608, 618, 619, 611, 568/607, 609

[56] References Cited

U.S. PATENT DOCUMENTS 3,293,193  12/1966  Krahler et al. ................ 568/608 X

FOREIGN PATENT DOCUMENTS 0770073  3/1957  United Kingdom ................ 568/608

Primary Examiner—Bernard Helfin
Attorney, Agent, or Firm—Bernhard R. Swick

[57] ABSTRACT

The instant invention relates to a process which comprises modifying a conventional polyoxyalkylene polyol by capping all the hydroxyl groups of the polyol with benzyl, aryl, substituted benzyl, substituted aryl or alkyl groups having 1 to 4 carbon atoms. This process comprises reacting the conventional polyoxyalkylene polyol with an alkali metal methoxide followed by reaction with an alkali metal hydride which in turn is followed by reaction with an organic halide.

18 Claims, No Drawings

PREPARING CAPPED POLYOXYALKYLENE POLYOLS

BACKGROUND OF THE INVENTION

The instant invention relates to a process for preparing capped polyoxyalkylene polyols.

Etherification or capping of a polyoxyalkylene compound having at least one terminal hydroxyl group has to date generally been effected by reacting the polyoxyalkylene compound with an alkali metal or its hydride such as sodium metal, potassium metal, sodium hydride or potassium hydride or sodium or potassium methoxide followed by reaction with an organic halide. Reaction with sodium methoxide is followed by removal of methanol produced by the reaction of the hydroxyl end groups with the alkali metal methoxide. However, the reaction eventually stops due to an equilibrium shift that does not favor methylation of the polymer. If the polymer is treated with methyl chloride at this point, the product would not be fully methyl capped.

If the polymer is reacted with sodium hydride rather than sodium methoxide prior to reaction with the organic halide, problems are presented due to the extremely high reactivity of the sodium hydride.

U.S. Pat. No. 3,507,923 discloses a method of capping allyl endblocked oxyalkylene polymers by reacting the polymer with sodium or potassium methylate (methoxide) followed by reaction with methyl chloride.

U.S. Pat. No. 4,046,702 describes treatment of polyoxyalkylated alcohol with sodium hydride or sodium methoxide prior to sulfating while U.S. Pat. No. 3,954,639 discloses treatment of an oxyalkylated alcohol or phenol with sodium hydride prior to sulfating.

U.S. Pat. No. 3,231,619 discloses the use of sodium hydride and sodium alkoxides among many other sodium compounds as a catalyst for oxyalkylating.

Accordingly it is the purpose of the instant invention to provide a method for purification or capping of polyoxyalkylene compounds wherein 95 to 100 percent capping is achieved by an easily controllable reaction in a relatively easy economical and safe manner.

SUMMARY OF THE INVENTION

The instant invention relates to a process which comprises modifying a conventional polyoxyalkylene polyol by capping all the hydroxyl groups of the polyol with benzyl, aryl, substituted benzyl, substituted aryl or alkyl groups having 1 to 4 carbon atoms. This process comprises reacting the conventional polyoxyalkylene polyol with an alkali metal methoxide followed by reaction with an alkali metal hydride which in turn is followed by reaction with an organic halide.

DESCRIPTION OF THE PREFERRED EMBODIMENT

In a preferred embodiment of the instant invention, the polyoxyalkylene polyol is prepared by capping all the hydroxyl groups of a conventional polyoxyalkylene polyol with benzyl, aryl, substituted benzyl, substituted aryl groups or alkyl groups having 1 to 4 carbon atoms. The conventional polyoxyalkylene polyol can be an ethylene oxide, propylene oxide or butylene oxide homopolymer or a heteric or block copolymer of ethylene oxide and at least one lower alkylene oxide having 3 to 4 carbon atoms. In a preferred embodiment, the ethylene oxide, constitutes at least about 10 percent by weight based on the total weight of the polyoxyalkylene polyol. In a most preferred embodiment about 10 to 80 percent by weight ethylene oxide is utilized with about 90 to 20 percent by weight of the lower alkylene oxide having 3 to 4 carbon atoms.

The polyoxyalkylene polyol capped with benzyl, aryl or $C_1$ to $C_4$ alkyl group is believed to have the following generalized formula:

$$R(A)_mOR$$

wherein A is an oxyalkylene group selected from oxyethylene, oxypropylene, oxybutylene, oxytetramethylene and heteric and block mixtures thereof; m is a whole number selected to give an overall average molecular weight of the product of 500 to 15,000, R is selected from the group consisting of benzyl, aryl, substituted benzyl, substituted aryl and $C_1$ to $C_4$ aliphatic groups and wherein the R groups may be the same or different.

In a preferred embodiment A comprises oxyethylene groups and groups selected from oxypropylene and oxybutylene. In a most preferred embodiment the oxypropylene or oxybutylene groups are centrally located with oxyethylene groups attached at each end thereof. The benzyl, aryl or alkyl caps are attached to the ends of the oxyethylene groups opposite the oxypropylene or oxybutylene groups. In another most preferred embodiment the oxyethylene groups are centrally located in the molecule and the oxypropylene or oxybutylene groups are attached at opposite ends of the oxyethylene groups. The benzyl, aryl or alkyl caps are attached to the ends of the oxypropylene or oxybutylene groups opposite the ends attached to the oxyethylene groups.

The conventional polyether polyols which are capped to produce the above described product are generally prepared utilizing an active hydrogen-containing compound having 1, 2, 3 or more active hydrogens in the presence of an acidic or basic oxyalkylation catalyst and optionally an inert organic solvent at elevated temperatures in the range of about 100° C. to 150° C. under an inert gas pressure generally from about 20 to about 100 pounds per square inch gauge. As an initiator, the compound containing an active hydrogen can be any compound containing at least one OH group, preferably an alkyl, aryl or arylalkyl alcohol, and most preferably an alkyl or arylalkyl compound, all with about 1 to 18, preferably about 1 to 12, and most preferably about 1 to 6 carbon atoms in the alkyl chain. Suitable initiators are selected from any compounds containing one or more OH groups having about 1 to 18 carbons and include aliphatic monofunctional alcohols. These can be used either alone or in mixtures. Representative alcohols include methyl, ethyl, propyl, butyl, amyl, hexyl, heptyl, octyl, nonyl, decyl, dodecyl, tetradecyl, cetyl and corresponding secondary and tertiary alcohols and mixtures thereof. Representative aryl initiators include phenol, cresol, xylol, octylphenol, and nonylphenol. Preparation of suitable polyoxyalkylene polyols is disclosed in U.S. Pat. Nos. 2,674,619; 2,677,700; 3,036,118; 2,838,345; 4,326,977; 2,425,755; British Patent No. 722,746 and Block and Graft Copolymerization, vol. 2, edited by R. J. Ceresa, pages 68 and 69, John Wiley & Sons copyright 1976.

The starting material may also be a polyether polyol which is capped on one end only. Such products are well known to those skilled in the art and the method of capping on one end only accordingly will not be described herein. Evidence of the fact that such products are well known to those skilled in the art is provided by U.S. Pat. No. 4,301,083, Formula II-c, at the top of column 4 thereof. Accordingly it is believed that the starting material for the process of the instant invention has the following generalized formula $$Q(A)_mOH$$

wherein Q is either H or R as defined above and A is the same as defined above.

The polyether polyols are reacted with an alkali metal alkoxide having 1 to 3 carbon atoms followed by reaction with an alkali metal hydride and finally by reaction with an organic halide having the structural formula $$RX$$

wherein X is a halogen and R is as previously defined. Preferably R is a $C_1$ to $C_4$ aliphatic group. Where the starting compound is a polyoxyalkylene compound capped on one end only, i.e., where Q is R, a conventional process for producing such compound involves reaction of the benzyl, aryl, or alkyl compound in the presence of sodium or potassium hydroxide. However, there is no potassium hydroxide in the final product that is used as the starting polyether polyol for this invention. The reactions according to the process of the invention described above are carried out in the absence of alkali metal hydroxide or appreciable amounts of water.

By the use of both alkali metal alkoxide particularly alkali metal methoxide, propoxide, or butoxide followed by reaction with alkali metal hydride prior to reaction with the organic halide it is possible to achieve 95 to 100 percent capping of the polyoxyalkylene polyol with safety and without the necessity of a carefully controlled and usually slow reaction, in order to achieve this goal. In accordance with the instant invention, the starting polyether polyol is stripped under vacuum to remove all impurities. For example in the case of a partially capped polyether and more specifically a straight chain polyol having only one cap on one end and a hydroxyl group on the other, which was initially prepared in the presence of an alkali metal hydroxide, the stripping will remove the alkali metal hydroxide and any water present. The vacuum is then relieved with nitrogen. The alkali metal alkoxide is then added in a sufficient mole ratio to react with from 50 to 95 percent of the hydroxyl groups of the material to be capped. The employment of an excess helps to guarantee the maximum amount of capping in this step, thereby leaving a minimum amount for further reaction with sodium hydride. The sodium methoxide employed is preferably dry and fresh. Reaction is performed until the maximum amount of capping is achieved, which generally requires about 30 minutes at atmospheric pressure. The temperature should range from about 100° to 175° C. The overall time would range from about 10 to 60 minutes. The vacuum is then applied to remove the methanol from the reaction of the hydroxyl end group or groups of the polyether with the alkali metal alkoxide. Eventually the reaction stops due to an equilibrium shift that does not favor metalation of the polymer. This occurs generally after about 2 hours of stripping at about 100° to 175° C. and about 0.1 to 10 millimeters of mercury. The optimum is about 120° C. and 5 millimeters of mercury. If the polymer were treated with the organic halide at this point the product would not be fully capped.

The sodium hydride is then added to the stripped reaction product at a temperature of about 20° to 120° C. and in an amount slightly in excess of the amount needed to cap all the remaining uncapped hydroxyl groups whereby all hydroxyl groups would be alkylated. Generally an excess of 1 to 5 percent of the volumetric amount is preferred.

The organic halide is then added to the reaction product at a temperature that should not be greater than 110° C. during addition as the unreacted organic halide will volatilize. Preferred temperature during addition is 90 to 110° C. Following addition, the reaction temperature could range from 50 to 150° C., however the reaction would probably take place at less than 50° C. In general the pressure would range from about 1 to 5 atmospheres.

The resulting product can be recovered from the reaction mixture by conventional methods and procedures for separation.

Depending on the type of their terminal groups, the capped polyoxyalkylene derivatives produced by the process of the instant invention are useful as surface active agents, solvents, solubilizing agents for inorganic salts, accelerators or catalysts for ionic organic reactions. These products are particularly useful for lubricating synthetic textile fibers such as polyester, nylon, poly(benzimdiazole), carbon and glass fibers.

The following examples further illustrate the various aspects of the invention. Where not otherwise specified throughout this specification and claims, temperatures are indicated in degrees centigrade and parts percentages and proportions are by weight.

EXAMPLE 1

Into a one liter, four necked, round bottom flask, equipped with a thermometer, reflux condenser and a mechanical stirrer were placed 234.2 parts of a polyoxyethylene polyoxypropylene block copolymer having the following formula:

$$HO(C_2H_4O)_m(C_3H_6O)_n(C_2H_4O)_nH$$

and having a molecular weight of the polyoxypropylene hydrophobe (m) of 1866 and containing 10 percent by weight oxyethylene groups. This was stripped at a temperature beginning at 23° C. and rising to 70° C. at 0.1 mm of Hg for 30 minutes after which the mixture was cooled to room temperature at atmospheric pressure. It was then heated to 120° and 14.2 parts of sodium methoxide added at atmospheric pressure. Vacuum was then applied bringing the pressure down to 0.1 mm Hg during which foaming was noted and the temperature was allowed to drop to 70°. The vacuum was then broken and it was allowed to return to atmospheric pressure after which methanol was stripped out at 0.1 mm Hg and 70° to remove 6.3 parts of methanol. The temperature was then increased to 120° and 1.4 parts of additional methanol recovered after which the pressure was returned to atmospheric. 0.5 parts of sodium hydride were then added and the mixture reheated to 110° after which methyl chloride was added in amount of 12.6 parts and refluxed at a temperature of 120° for one hour and fifteen minutes. The mixture was then allowed to cool after which excess methyl chloride was stripped off. The product was then treated with 2 percent deionized water and 4 percent Magnesol for 60 minutes at 98° C., filtered, and stripped. The resulting product was a dimethyl ether of the polyoxyethylene-polyoxypropylene glycol described above which was 96.3 percent methyl capped as determined by hydroxyl number.

EXAMPLE 2

Into a one liter, four necked, round bottom flask, equipped with a thermometer, reflux condenser and a mechanical stirrer were placed 240 parts of a monomethylether of a polyoxyethylene polyoxypropylene block copolymer having the following formula:

$$CH_3O(C_2H_4O)_m(C_3H_6O)_n(C_2H_4O)_nH$$

and having a molecular weight of the polyoxypropylene hydrophobe (m) of 1100 and containing 15 percent by weight oxyethylene groups. This was stripped at a temperature beginning at 23° C. and rising to 90° C. at 0.1 mm of Hg for 40 minutes after which the mixture was cooled to room temperature at atmospheric pressure. It was then heated to 120° cooled to 70° C. and 13.5 parts of sodium methoxide added at atmospheric pressure. Vacuum was then applied bringing the pressure down to 0.1 mm Hg. The vacuum was then broken and it was allowed to return to atmospheric pressure after which methanol was stripped out at 0.1 mm Hg and 120° to remove 7.5 parts of methanol after which the pressure was returned to atmospheric. 1.6 parts of sodium hydride were then added and the mixture reheated to 120° after which methyl chloride was added in amount of 11.9 parts and refluxed at a temperature of 120° for one hour and thirty minutes. The mixture was then allowed to cool after which excess methyl chloride was stripped off. The product was then treated with 2 percent deionized water and 4 percent magnesol for 60 minutes at 98° C., filtered, and stripped. The resulting product was a dimethyl ether of the polyoxyethylene-polyoxy-propylene glycol which was 100 percent methyl capped as determined by hydroxyl number.

EXAMPLE 3

A polyamide polymer is fed into a screw extruder and heated to 275° C. The molten polymer is pumped under pressure of approximately 1700 psig through a sand filter and then through the capillary of a spinnerette plate. Freshly extruded filaments are put through a descending spinning tower into which air of 70° F. temperature and 65 percent relative humidity is admitted. Filaments are gathered into yarn and, upon emerging from the spinning tower, coated with fiber lubricant using a finish applicator (described in U.S. Pat. No. 3,347,207). The fiber lubricant is substantially pure dimethylether of an ethylene oxide, propylene oxide block copolymer produced according to Example 1 having the following formula:

$$CH_3O(C_2H_4O)_n(C_3H_6O)_m(C_2H_4O)_nCH_3$$

wherein m plus n is sufficient to give a total molecular weight of 1866 and wherein m and n are of sufficient value whereby the percentage of ethylene oxide groups is 10 percent. The lubricant coating is applied to the yarn at a rate of 0.75 weight percent based on the weight of the yarn. The yarn is then wound into a package at a rate of about 2000 feet per minute. The resulting yarn is drawn over a one inch diameter draw pin at a delivery rate of 1536 feet per minute during which time the yarn passes over a heater maintained at 175° C. The yarn is then heat cured (employing an electric heater at 150° C. for 30 minutes) to polypropylene carpet backing with a latex binder. The dimethylether lubricant has a relatively low viscosity and is characterized by a minimum of interaction with the polyurethane elastomers used in the fiber processing machinery.

The embodiments of the invention in which an exclusive privilege or property is claimed are defined as follows:

1. A process for preparing a capped polyoxyalkylene polyol having the structural formula:

$$R(A)_mOR$$

wherein A is an oxyalkylene group selected from oxyethylene, oxypropylene, oxybutylene, oxytetramethylene and heteric and block mixtures thereof; m is a whole number selected to give an overall average molecular weight of the product of about 500 to 15,000 and R is selected from the group consisting of benzyl, aryl, substituted benzyl, substituted aryl, and $C_1$ to $C_4$ aliphatic groups and wherein the R groups may be the same or different which process comprises:

reacting a polyoxyalkylene compound having the structural formula:

$$Q(A)_mOH$$

wherein Q is H or R and A and m are as previously defined with an alkali metal alkoxide followed by reaction with an alkali metal hydride followed by reaction with an organic halide having the formula:

$$RX$$

wherein X is a halide and R is as previously defined.

2. The process of claim 1 wherein A is a heteric or block mixture of oxyethylene and oxypropylene groups and said polyoxyalkylene compound is reacted with said alkali metal methoxide at a temperature of about 100° to 175° C. and a pressure of about 0.1 to 10.0 mm of mercury followed by reaction with said alkali metal hydride at a temperature of about 20° to 120° C. followed by reaction with said organic halide at a temperature of about 50° to 150° C. and a pressure of about 1 to 5 atmospheres.

3. The process of claim 2 wherein said alkali metal alkoxide is the reaction product of an alkali metal and a $C_1$ to $C_3$ alkylene oxide.

4. The process of claim 3 wherein said alkali metal alkoxide is a sodium or potassium alkoxide and said alkali metal hydride is sodium or potassium hydride.

5. The process of claim 4 wherein said alkali metal alkoxide is sodium alkoxide and said alkali metal hydride is sodium hydride and R is a $C_1$ to $C_4$ aliphatic group.

6. The process of claim 5 wherein said alkali metal alkoxide is sodium methoxide and said organic halide is methyl chloride.

7. The process of claim 1 wherein Q is R.

8. The process of claim 7 wherein A is a heteric or block mixture of oxyethylene and oxypropylene groups and said polyoxyalkylene compound is reacted with said alkali metal methoxide at a temperature of about 100° to 175° C. and a pressure of about 0.1 to 10.0 mm of mercury followed by reaction with said alkali metal hydride at a temperature of about 20° to 120° C. followed by reaction with said organic halide at a temperature of about 50° to 150° C. and a pressure of about 1 to 5 atmospheres.

9. The process of claim 8 wherein said alkali metal alkoxide is the reaction product of an alkali metal and a $C_1$ to $C_3$ alkylene oxide.

10. The process of claim 9 wherein said alkali metal alkoxide is a sodium or potassium alkoxide and said alkali metal hydride is sodium or potassium hydride.

11. The process of claim 10 wherein said alkali metal alkoxide is sodium alkoxide and said alkali metal hydride is sodium hydride and said organic halide R is a $C_1$ to $C_4$ aliphatic group.

12. The process of claim 11 wherein said alkali metal alkoxide is sodium methoxide and said organic halide is methyl chloride.

13. The process of claim 1 wherein Q is H.

14. The process of claim 13 wherein A is a heteric or block mixture of oxyethylene and oxypropylene groups and said polyoxyalkylene compound is reacted with said alkali metal methoxide at a temperature of about 100° to 175° C. and a pressure of about 0.1 to 10 mm of mercury followed by reaction with said alkali metal hydride at a temperature of about 20 to 120° C. followed by reaction with said organic halide at a temperature of about 50 to 150° C. and a pressure of about 1 to 5 atmospheres.

15. The process of claim 14 wherein said alkali metal alkoxide is the reaction product of an alkali metal and a $C_1$ to $C_3$ alkylene oxide.

16. The process of claim 15 wherein said alkali metal alkoxide is a sodium or potassium alkoxide and said alkali metal hydride is sodium or potassium hydride.

17. The process of claim 16 wherein said alkali metal alkoxide is sodium alkoxide and said alkali metal hydride is sodium hydride and R is a $C_1$ to $C_4$ aliphatic group.

18. The process of claim 17 wherein said alkali metal alkoxide is sodium methoxide and said organic halide is methyl chloride.

* * * * *